United States Patent [19]

Fritschi

[11] Patent Number: 4,605,552

[45] Date of Patent: Aug. 12, 1986

[54] CALCIUM-ANTAGONIST COMPOSITIONS INTENDED FOR INHALATION AND PROCESS FOR THEIR MANUFACTURE

[75] Inventor: Edgar Fritschi, St. Peter, Fed. Rep. of Germany

[73] Assignee: Warner-Lambert Company, Morris Plains, N.J.

[21] Appl. No.: 631,049

[22] Filed: Jul. 16, 1984

[30] Foreign Application Priority Data

Jul. 20, 1983 [DE] Fed. Rep. of Germany ....... 3326089

[51] Int. Cl.$^4$ .................. A61L 9/04; A61K 31/55
[52] U.S. Cl. .................................. 424/45; 514/211
[58] Field of Search ................. 424/45, 266; 514/211

[56] References Cited

U.S. PATENT DOCUMENTS

| | | | |
|---|---|---|---|
| 3,014,844 | 12/1961 | Thiel et al. | 424/46 |
| 3,106,511 | 10/1963 | Cuttler et al. | 424/45 |
| 4,447,449 | 5/1984 | Marshall | 424/283 |

FOREIGN PATENT DOCUMENTS 1132933 6/1968 United Kingdom .

OTHER PUBLICATIONS

Flaim et al. (Ed), "Comparative Pharmacology of Calcium Blockers Based on Studies of Output Distribution", *Calcium Blockers*, Urban & Schwarzenberg publishers, pp. 179-192 (1982).
Chem. Abst. 97: 16919v (1982)—Malo et al.
Chem. Abst. 98: 137459z (1983)—Brugman et al.
Chem. Abst. 100: 150862e (1984)—Krivoy et al.

*Primary Examiner*—Douglas W. Robinson
*Attorney, Agent, or Firm*—Ronald A. Daignault

[57] ABSTRACT

Pharmaceutical compositions for administration by inhalation, wherein calcium-antagonists are employed as the active substances, e.g., metered-sprays of calcium-antagonists, in particular of diltiazem and a process for their manufacture are described.

2 Claims, 5 Drawing Figures

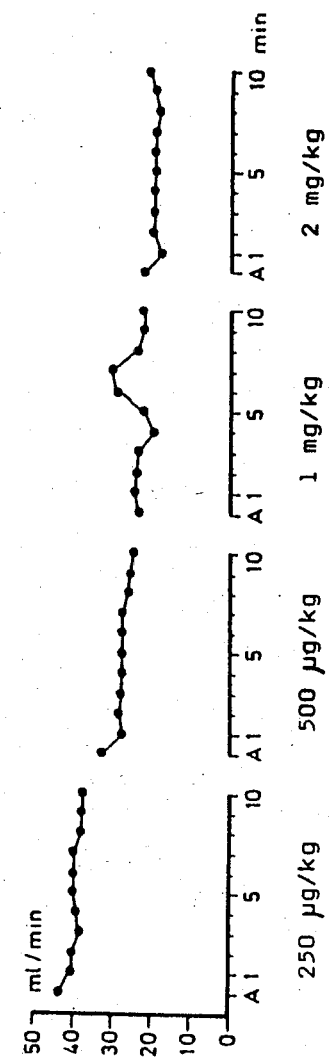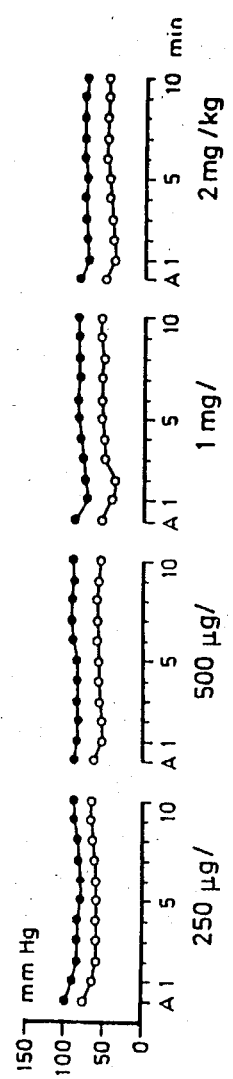
Fig.1d
Fig.1e

CALCIUM-ANTAGONIST COMPOSITIONS INTENDED FOR INHALATION AND PROCESS FOR THEIR MANUFACTURE

BACKGROUND OF THE INVENTION

Long-term therapy for angina pectoris is nowadays usually conducted with nitrates such as isosorbide-dinitrate or isosorbide-mononitrate, or with calcium antagonists.

Cutting short an acute angina pectoris attack proves considerably more difficult, since the named active substances only allow an immediate onset of action with i.v. administration. Furthermore, this can only be carried out by the doctor, who is in most cases not at hand when the angina pectoris attack occurs. A further disadvantage of parenteral treatment is that it can easily lead to postural hypotension in the case of calcium-antagonists on account of strong peripheral side-effects upon rapid absorption.

At present the sublingual or inhalation administion of nitroglycerin is the only practicable solution open to the patient for treating the attack, since this active substance can take an immediate effect on account of its physiochemical properties and its special pharmacological profile.

Since the specialist has hitherto not made therapeutic use of the immediate onset of action of calcium antagonists, in the knowledge of the strong peripheral effect of this active substance class, practically only nitroglycerin remained for treating acute cases, but with nitroglycerin one has to reconcile to side-effects such as nausea, dizziness, tachycardia, and a sudden drop in blood pressure.

It has surprisingly been found that calcium-antagonists are immediately effective upon inhalational administration and cause an immediate increase in the blood flow in the coronary artery without exerting an unfavorable influence on the periphery.

Thus calcium-antagonists are unexpectedly suitable for therapy of angina pectoris attacks when administered by inhalation. They have the great advantage as compared with the therapy known hitherto that the side-effects of nitroglycerin are avoided and the described activity of calcium-antagonists, which are concededly drugs of first choice in influencing the pathophysiological condition, can also be made use of in acute attacks.

SUMMARY OF THE INVENTION

Accordingly, the present invention provides a pharmaceutical composition for administration by inhalation comprising an inhalation propellant or carrier and an effective amount of at least one active substance for treating angina pectoris, wherein the active substance is a calcium-antagonist.

Another subject matter of the invention is a process for the preparation of a pharmaceutical for the treatment of an angina pectoris attack which provides immediate onset of action, characterized in that as the active substance a calcium-antagonist in solid or liquid form is incorporated in an inhalation propellant or carrier, and that the propellant or carrier together with the active substance is filled off under pressure, or by cooling below the boiling point of the propellant or carrier, into an inhalation receptacle suitable for the inhalation of pharmaceuticals thus prepared, which receptacle is then fitted with a gastight seal.

The invention further provides a method for treating angina pectoris which comprises administering to a host suffering therefrom an effective amount of a calcium-antagonist by inhalation means.

DETAILED DESCRIPTION

Figure 1A:
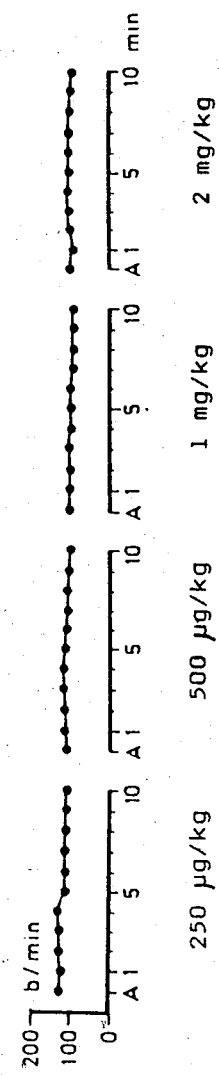

Well-known calcium-antagonists are, e.g., nifedipine, verapamil, etafenone, prenylamine, perhexiline, and gallopamil. Diltiazem is preferred within the framework of this invention as being particularly suitable for the new therapy form.

The active substances, as long as they are soluble in water, such as, for example diltiazem.HCl, can be added to an aqueous solution and filled under pressure into a spray container with nitrogen.

A preferred method is to mix the active substance and a suspension auxiliary, such as, for example sorbitan triolate at approximately 5°–20° C. with a fluorocarbon hydride which is liquid at this temperature, to transfer this mixture together with the safety propellant mixture (fluorocarbon hydride: 12:114) into the spray container by means of the cold drawing-off process and to seal the same immediately.

Another possibility would be to fill the active substance in micronized form, i.e., having a particle diameter of between 0.5 and 5 $\mu$m, together with a corresponding finely-dispersed inhalable carrier such as lactose into a hard gelatin capsule and to conduct the therapeutic application using a normal mechanical powder-inhaler.

The dosage of the inhaler should be adjusted in such a way that a one-time dose for adults lies between 5 and 50 mg.

The following Examples are given for the purpose of illustrating the invention:

EXAMPLE 1

1.632 kg diltiazem.HCl (micronized) are mixed with 500 g sorbitan trioleate and 37.42 Freon ® 11, at a temperature of approximately 10° C. and suspended disagglomerating. The suspension thus obtained is subsequently added to 170.45 kg safety propellant mixture (Fluorocarbonhydride 12:114) at a temperature of −50° C. and the mixture homogenized. It is then filled into aluminum cans in the cold, which are then sealed immediately with a metered-dosage valve.

10,000 cans (effective contents 22 ml) are thus obtained for 300 puff a 250 $\mu$l corresponding to 0.544 mg diltiazem.HCl active substance/puff.

EXAMPLE 2

544 g diltiazem.HCl (micronized) are homogeneously mixed with 4.456 kg lactose (micronized) and filled into hard gelatin capsules with an active substance content of 5.44 mg diltiazem.HCl (corresp. to 5 mg base).

The capsules can be perforated using a powder inhaler, so that the contents of the capsules can be inhaled.

The following trials were conducted to prove the efficacy of the new administration forms.

The test animals were two mongrel dogs (females, body weight 16 and 18 kg) under pentobarbital anesthesia (30 mg/kg i.v. initial). The animals were tracheotomized and were supplied with oxygen via a Y-shaped tracheal cannula, one branch of which served to carry out substance insufflation, using an Engstrom respirator (type ER 300) with ambient air.

The following parameters of the animals were measured:
1. ECG leg lead II
2. Heart rate (R zig-zags triggered from ECG) using a pulse rate meter (in beats/min).
3. Arterial blood pressure in the right femoral artery using a tip catheter (in mmHg).
4. The left ventricular heart pressure using a tip catheter via right carotid artery (in mmHg).
5. The contractility of the heart using an HSE differentiator from the isometric part of the left ventricular pressure curve, differentiated as $dp/dt_{max}$ (in mmHg/sec).
6. The blood flow in the left femoral artery using electromagnetic measurement of flow (in ml/min).
7. The blood flow in the left descending coronary artery.

All parameters were continuously recorded simultaneously using a direct recorder and evaluated and printed out 1, 5, and 10 minutes, respectively after application.

The substance was applied using a compressed air metered-spray resembling a pistol. The weight-specific quantity of the original substance was filled into the outlet pipe of the metered-spray from the front and completely insufflated into the trachea of the animal at a pressure of 0.2 atmosphere above atmospheric pressure during the pump-controlled inspiration. The insufflation procedure lasts one second in each case and, as has been found in previous trials, does not alone have any influence whatsoever on the circulation sizes measured.

Figure 1B:
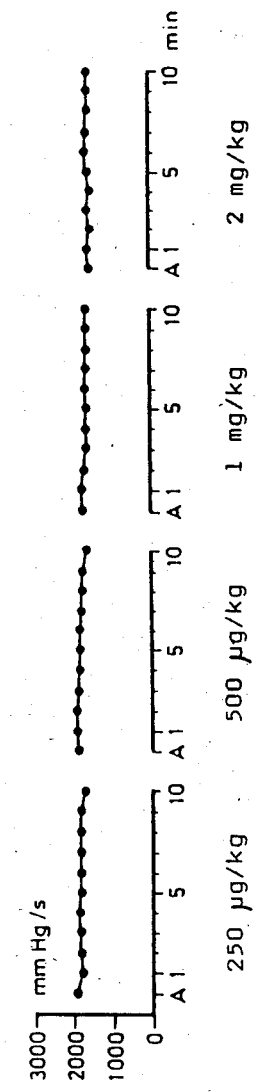
Figure 1C:
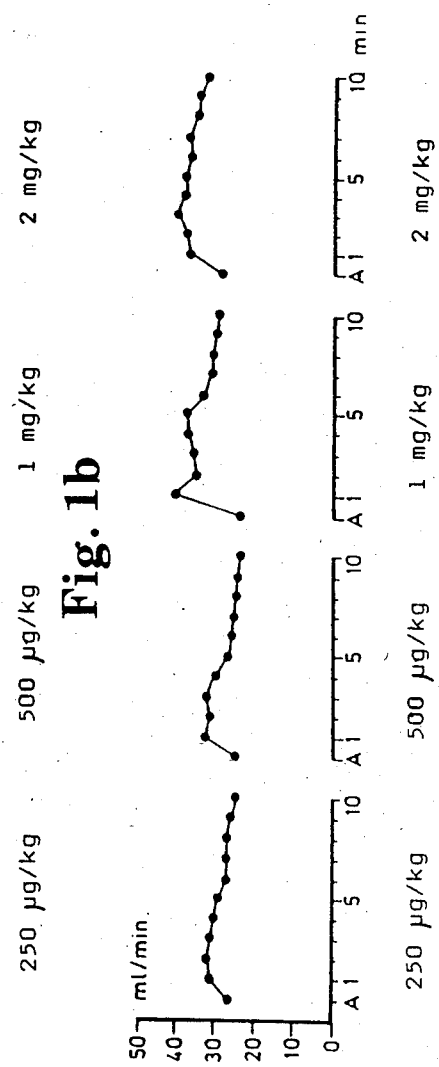

The results of the trials are represented in FIG. 1. It can be deduced from the curves that neither the heart rate nor the contractility are influenced, but that the flow in the coronary artery is dose-dependent and increases immediately for a sustained period.

Further, it can be seen that the arterial blood pressure only decreases marginally subsequent to high doses and then only distinctly after influencing the coronary flow.

I claim:

1. A method for treating angina pectoris which comprises administering to a patient in need thereof, by inhalation, an antianginal effective amount of the calcium antagonist diltiazem.

2. The method of claim 1 wherein the calcium-antagonist is diltiazem hydrochloride.

* * * * *